United States Patent
Dominguez et al.

(10) Patent No.: US 10,039,246 B2
(45) Date of Patent: Aug. 7, 2018

(54) MACHINE HARVESTABLE TOMATILLO

(71) Applicant: Vilmorin & Cie, Paris (FR)

(72) Inventors: Flavio Ramos Dominguez, Sinaloa (MX); Joseph Patrick Jacobs, Davis, CA (US)

(73) Assignee: Vilmorin & Cie, Paris (FR)

( * ) Notice: Subject to any disclaimer, the term of this patent is extended or adjusted under 35 U.S.C. 154(b) by 426 days.

(21) Appl. No.: 14/731,885

(22) Filed: Jun. 5, 2015

(65) Prior Publication Data

US 2016/0353680 A1 Dec. 8, 2016

(51) Int. Cl.
*A01H 5/08* (2018.01)
*A23L 19/00* (2016.01)

(52) U.S. Cl.
CPC ............. *A01H 5/08* (2013.01); *A23L 19/00* (2016.08)

(58) Field of Classification Search
None
See application file for complete search history.

(56) References Cited

U.S. PATENT DOCUMENTS 7,921,628 B2 * 4/2011 Meester ............... A01D 45/006
171/27

OTHER PUBLICATIONS

Tomatillo, Wikipedia page edited Jul. 23, 2017.*
Mulato-Brito et al 2007 Vegetable Crops Research Bulletin 66: 117-127.*
Edelman et al May 2014 HortScience 49(5): 628-636.*
Wildrose Heritage Seed Company Tomatillo—Rio Grande Verde 2016 web page.*
Jackson 2013, The Star-Ledger, NJ Advance Media.*

* cited by examiner

*Primary Examiner* — David H Kruse
(74) *Attorney, Agent, or Firm* — Cooley LLP (57) ABSTRACT

The present invention provides tomatillo ideotypes and tomatillo plants with machine harvestable traits combined with desirable agronomic traits. The present invention also provides methods of making such plants and methods of using such plants to produce additional machine harvestable tomatillo plants.

20 Claims, 4 Drawing Sheets

MACHINE HARVESTABLE TOMATILLO

TECHNICAL FIELD

The present invention relates to plant breeding and methods of agronomical and horticultural production. More specifically, the present invention relates to agriculturally useful tomatillo plants that are specifically bred for mechanical harvesting and to methods of producing, processing and using such plants and their parts, including their fruits.

BACKGROUND

Existing tomatillo varieties are suitable for manual harvesting, which often requires growers to send crews into the field multiple times. It is known that labor cost for manual harvest for tomatillo is much higher than labor cost for mechanical harvest. A tomatillo plant must possess specific attributes for mechanical harvesting. Currently, there are no genotypes that have been specifically bred for mechanical harvesting for many of the commercially important tomatillo varieties. Existing varieties have indeterminate growth habit resulting in continuous fruit set.

Tomatillos are used in Mexican cuisine. Tomatillos are purchased at mature green ripe stage, a stage were fruits are highest in acids and lower in sugars. Fruit are then de-husked and boiled with salt and other spices until soft. Once soft they are pureed into a salsa with hot green chiles. Although households and restaurants are the greatest manufacturers and consumers of tomatillo green salsa, a growing processing industry does exist. Processors buy fruits from growers or suppliers and then process. Typically, processors buy tomatillo fruits without the husk on the fruit, requiring the grower or middle market to remove the husk. This step adds cost to the tomatillo producers.

The present invention invention provides growers with two immediate benefits. There is indeed a need for having concentrated set varieties producing more yield in less time and being machine harvestable. Grower inputs and fruits exposure to pests are reduced. Moreover, there is also a need to have tomatillos allowing growers to grow tomatillos directly for processors. Fruits can be machine harvested without the husk, reducing the cost to de-husk the fruit before sending them to the market.

The current invention meets a long felt need for a tomatillo plant ideotype suitable for machine harvesting and provides new tomatillo plants useful for mechanical harvesting combined with other highly desirable agronomic traits.

SUMMARY OF THE INVENTION

The present invention provides machine harvestable tomatillo plants or parts thereof wherein said plant has (i) a determinate growth habit, (ii) a bush type growth habit, and (iii) an early concentrated fruit set ideotype.

In some embodiments, said bush type growth habit comprises (i) a plant height of at most 60 cm at maturity, and (ii) a mean branch length of at most 100 cm at maturity.

In some embodiments, said early concentrated fruit set ideotype comprises (i) at least 70% of mature fruits at 100 days after sowing, (ii) an harvest time comprised between 80 and 130 days after sowing, (iii) a tomatillo yield at least 2.5 times higher than the tomatillo yield of a non-early concentrated variety at 100 days after sowing, and/or (iv) a cumulative number of tomatillo fruits at least 5 times higher than the cumulative number of tomatillos of a non-early concentrated variety at 120 days after sowing.

In some embodiments, the machine harvestable tomatillo plant according to the invention further comprises at least 2 times more tomatillos with open husk than a non-early concentrated variety at maturity.

In one embodiment of the present invention, the machine harvestable tomatillo plants of present invention are of the species *Physalis philadelphica Lam.*, also known as *Physalis ixocarapa*.

The present invention provides methods of harvesting tomatillo fruit comprising using a machine to harvest the fruit of tomatillo plants grown in a field until ready for harvesting of the fruit, wherein the tomatillo plants are the machine harvestable tomatillo plants of the present invention. The present invention further provides such methods where the harvesting machine is a tomato harvesting machine. In addition, the present invention provides such methods wherein the tomatillo field is at least one half acre in size.

In some embodiments, the present invention provides tomatillo plants designated 'TCS1', and 'TOH1' or part thereof, a representative sample of the seeds of which have been deposited under NCIMB Accession Numbers 42413 and 42412, respectively. The present invention provides the seed, ovules, pollen or fruit of the tomatillo plants of the present invention. The present invention further provides tomatillo plants having all of the morphological and physiological characteristics of the machine harvestable tomatillo plants of the present invention, e.g. tomatillo plants having all of the morphological and physiological characteristics of the machine harvestable tomatillo plants TCS1 or TOH1. The present invention provides the seed, ovules, pollen or fruit of tomatillo plants having all of the morphological and physiological characteristics of the machine harvestable tomatillo plants of the present invention, e.g. tomatillo plants having all of the morphological and physiological characteristics of the machine harvestable tomatillo plants TCS1 or TOH1. The present invention further comprises offspring of the machine harvestable tomatillo plants of the present invention, said offspring having at least (i) a determinant growth habit, (ii) a bush type growth habit, and (iii) an early concentrated fruit set ideotype. In some embodiments, said offsprings further comprises at least 2 times more tomatillos with open husk than a non-early concentrated variety at maturity.

In some embodiments, the non-early concentrated variety is selected from the group consisting of Gran Esmerelda, Chapingo, Tecozautla and Tamayo R.

The present invention also provides for asexually reproduced tomatillo plants produced via asexual reproduction of the machine harvestable tomatillo plants of the present invention.

The present invention further provides regenerable tomatillo plant parts capable of producing a tomatillo plant having all of the morphological and physiological characteristics of the machine harvestable tomatillo plants of the present invention.

The present invention also provides tissue culture of regenerable cells produced from the machine harvestable tomatillo plants, or parts thereof, of the present invention. The present invention also provides machine harvestable tomatillo plants regenerated from a tissue culture of the plants, or parts thereof, of machine harvestable tomatillo plants of the present invention.

The present invention also provides methods for producing tomatillo seed. In some embodiments, the methods comprise crossing the machine harvestable tomatillo plants of the present invention with itself or another tomatillo plant, and harvesting the resultant seed. In some embodiments, the present invention further provides such methods which include growing the resultant seed to produce one or more progeny tomatillo plants. In some embodiments, the methods further comprise breeding from one or more of said progeny tomatillo plants to produce progeny seed. In some embodiments, the methods further comprise harvesting said progeny seed. In addition, the present invention provides such methods further comprising growing said progeny seed, breeding from the resultant tomatillo plants to produce seed, and harvesting said seed, over 1, 2, 3, 4, 5, 6 or more generations.

In some embodiments, the machine harvestable tomatillo plant according to the invention further comprises an internode length less than 7 cm and/or an average internode number of 15.

In some embodiments, the invention includes a fruit of the machine harvestable tomatillo of the present invention.

In some embodiments, the invention includes a seed of the machine harvestable tomatillo of the present invention.

In some embodiments, the machine harvestable tomatillo plant, is the tomatillo plant TCS1, or TOH1, for which a representative sample of the seed of which has been deposited under NCIMB Accession Number 42413, or NCIMB Accession Number 42412 respectively.

In some embodiments, the invention teaches the fruit or seed of the machine harvestable tomatillo plant TCS1, or TOH1, for which a representative sample of the seed of which has been deposited under NCIMB Accession Number 42413, or NCIMB Accession Number 42412 respectively.

In some embodiments the present invention teaches methods of breeding tomatillos comprising: (i) making a cross between a machine harvestable tomatillo plant of the present invention, with a second plant to produce a progeny plant. In some embodiments, the methods further comprise (ii) harvesting the resulting seed; wherein said seed is capable of germinating.

In some embodiments the invention teaches the tomatillo plants produced by the breeding method of the present invention.

In some embodiments, the present invention teaches a method of producing tomatillo fruits, said method comprising placing a seed from a machine harvestable tomatillo plant of the present invention in an environment conducive to germination. In some embodiments, the methods further comprise allowing said seed to germinate into a plant. In some embodiments, the methods further comprise allowing said plant to produce tomatillo fruits.

In some embodiments, the present invention teaches methods of harvesting the machine harvestable tomatillo plants of the present invention, said method comprising harvesting the fruit of a mature tomatillo plant using a harvesting machine. In some embodiments, the mature tomatillo plant that is harvested in the tomatillo plant according to the invention.

In some embodiments, the harvesting machine of the present invention is a tomato harvesting machine.

In some embodiments, the present invention also provides a food product obtained from a fruit of the machine harvestable tomatillo of the present invention. In some embodiments, said food product is selected from the group consisting of fresh fruits, pickled fruit and sauces.

BRIEF DESCRIPTION OF THE DRAWINGS

FIG. 1 compares means of three repetitions by ideotype harvested on four consecutive weeks.

FIG. 2 compares means of three repetitions by ideotype harvested on four consecutive weeks. The tomatillo plant according to the invention (1-concentrated) significantly out yield the check varieties (2-extended, i.e. non-early concentrated variety) for the first three weeks of harvest.

DETAILED DESCRIPTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom).

As used herein, the term "plant part" refers to any part of a plant including but not limited to the shoot, root, stem, seeds, fruits, leaves, petals, flowers, ovules, branches, petioles, internodes, pubescence, pollen, stamen, rootstock, scion and the like.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the term "transplanting" refers to standard tomatillo production practices. Growers purchase seeds and then grow them in flats prior to transplanting them to the field. Typically tomatillos are grown for 4-5 weeks in flats prior to transplant to the field. Plants ready for transplant may have between 3-5 true leaves.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "Resistance" is as defined by the ISF (International Seed Federation) Vegetable and Ornamental Crops Section for describing the reaction of plants to pests or pathogens, and abiotic stresses for the Vegetable Seed Industry.

Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

By "tolerance" it is meant the ability of a plant variety to endure biotic and abiotic stress without serious consequences for growth, appearance and yield.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "mass selection" refers to a form of selection in which individual plants are selected and the next generation propagated from the aggregate of their seeds. More details of mass selection are described herein in the specification.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self-pollinated" or "self-pollination" means the pollen of one flower on one plant is applied (artificially or naturally) to the ovule (stigma) of the same or a different flower on the same plant.

As used herein, the term "tomatillo" mainly refers to a plant species in the genus, unless specified otherwise. The term tomatillo as used herein refer to plant of the Solanaceae family from the species *Physalis philadelphica Lam*, also known as *Physalis ixocarpa*. Tomatillo is also known as the Husk Tomato or Mexican Husk Tomato. The tomatillo plant is of the nightshade family, related to the cape gooseberry, bearing small, spherical and green or green-purple fruit of the same name.

As used herein, the phrase "internode length" refers to the distance between two branching nodes.

By "open husk", it is meant that the husk (or calyx) is not closed around the fruit after pollination. Consequently, tomatillos with open husk can then fall easily of the plant without the closed husk (or calyx) at harvest.

As used herein, "maturity" refers to the mature green stage of tomatillos. Tomatillos have two states of maturity. One is physiological and corresponds to fruits that are turning from green to dull yellow (at that stage fruits are overmature for the market) and the other is based on human consumption and correspond to the mature green stage. For the purpose of the patent, the mature tomatillos are the ones that are consumed in the mature green stage, which is between about 10-30 days from physiological maturity. At mature green stage tomatillos have their highest levels of acidity. As they ripen the acidity decreases and sweetness increases. In some embodiments, maturity can be defined as the time when tomatillo fruit are green in color and if consumed have a bright or tart flavor. The standard used in the field with growers is typically when fruit are still bright green in color.

Tomatillo Plants for Machine Harvesting and Other Desirable Agronomic Traits

The present invention provides tomatillo plants which are machine harvestable.

In one embodiment, the machine harvestable tomatillo of the present invention have additional agronomic traits related to fruit which are selected from the group consisting of fruit shape, fruit weight, ripening date, fruit diameter, fruit length, pericarp thickness, soluble solids concentration, pedicel diameter, pedicel length, seed weight, firmness, and fruit color.

In further embodiments, the tomatillo plants of the present invention comprise one or more other agronomic traits. For example, such traits can be morphological traits (such as plant height, fruit phenotypes, branching habits, leaf shape, color of plant parts, variegated seedlings, flowers, immature fruit colors, mature fruit colors, transition of fruit colors), physiological traits (such as acid content and lycopene content), sterility traits (such as self-incompatibility and self-compatibility), and resistance to diseases, nematodes, and herbicides.

The present invention also provides a genetically related tomatillo plant population (progeny) derived from the tomatillo plants described herein. Such genetically related tomatillo plant population can be produced through either natural or artificial process, sexually or asexually, e.g., by cutting, grafting, layering, division, budding, grafting or tissue culture.

The present invention also provides a seed, a fruit, a plant population, a plant, a plant part, a plant cell and/or a plant tissue culture derived from the plants of the present invention. In one embodiment, the regenerable cells are derived from embryos, protoplasts, meristematic cells, callus, pollen, leaves, anthers, stems, petioles, roots, root tips, fruits, seeds, flowers, cotyledons, or hypocotyls.

The present invention also provides a cutting, a rootstock, a scion, or an explant from the tomatillo plants as described above for grafting.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. A detailed grafting method for example for *Capsicum* species is described by Toth et al., Kokalis-Burelle et al., 2009, and DeWitt and Bosland, 2009, each of which is incorporated by reference in its entirety.

The plants of the present invention can be used for many purposes. In one embodiment, a plant of the present invention is used as a donor plant of genetic material which can be transferred to a recipient plant to produce a plant with desired agronomic traits which has the machine harvestable traits of the present invention. Any suitable method known in the art can be applied to transfer genetic material from a donor plant to a recipient plant. In most cases, such genetic material is genomic material.

In one embodiment, the whole genome of the machine harvestable tomatillo plants of the present invention is transferred into a recipient plant. This can be done by crossing the plants to a recipient plant to create a F1 plant. The F1 plant can be further selfed and selected for one, two, three, four, or more generations. Selection pressures for certain desirable traits includes but are not limited to a resistance test, molecular marker selection, agronomic traits phenotype selection, or a combination thereof.

In some embodiments, the recipient plant is a tomatillo plant, or any other plants that can hybridize with the machine harvestable plants of the present invention.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, improved food quality, decrease in cracking, quicker color change when the fruit matures etc. Additional examples of agronomically important traits includes pest resistance, vigor, development time (time to harvest), enhanced nutrient content, novel growth patterns, flavors or colors, salt, heat, drought and cold tolerance, and the like.

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires.

In one embodiment, the recipient plants and/or lines have one or more preferred traits related to resistance/tolerance to pathogens, such as resistance to pests like whitefly, leaf miner, or aphids; to fungus like powdery mildew; to virus like cucumber mosaic virus (CMV), tobacco etch virus (TEV); to nematodes (Meloidogyne species for example), and/or to bacteria like bacteria of Pseudomonas or Xanthomonas species.

Machine Harvestable Traits

In some embodiments, the present invention teaches traits that are important for machine harvesting tomatillo plants. In some embodiments, the tomatillo plant according to the invention has (i) a determinate growth habit (ii) a bush type growth habit, and (iii) an early concentrated fruit set ideotype.

As used herein, the phrase "determinate growth habit" refers to a plant which has a definite growth: the axis being limited by the development of the terminal flower bud or other reproductive structure does not continue to elongate indefinitely. A determinate plant is a plant whose growth terminates while still under favorable growing conditions. It is opposed to an indeterminate plant whose growth continues while growing conditions are favorable. In one embodiment, the tomatillo plant ideotype of the present invention has determinate growth when compared to indeterminate growth of non-ideotype tomatillo plants.

As used herein the phrase "bush type growth habit" refers to the heritable vegetative growth habit of the tomatillo plant at maturity comprising (i) a plant height of at most 60 cm (but at least 40 cm), and (ii) a mean branch length of at most 100 cm (but at least 20 cm). A "non-bush" growth type is any other type, such as variety Gran Esmereida or Tamayo R or Chapingo or Tecozautla having a plant height significantly higher than 60 cm, and/or having a mean branch length of at least 110 cm.

As used herein the phrase "concentrated fruit set ideotype" refers to plants having synchronous flowering and fruit setting which concentrates the yield into a single harvest amenable to machine picking. In one embodiment, the tomatillo plant ideotype of the present invention has a more or greater concentrated fruit set when compared to the less or lack of concentrated fruit set for non-ideotype tomatillo plants. In one embodiment, the tomatillo plant ideotype of the present invention has an earlier concentrated fruit set when compared to the concentrated fruit set for non-ideotype tomatillo plants, i.e. for non-early concentrated tomatillo plants.

In some embodiments, said early concentrated fruit set ideotype comprises (i) at least 70% of mature fruits at 100 days after sowing, (ii) an harvest time comprised between 80 and 130 days after sowing, (iii) a tomatillo yield at least 2.5 times higher than the tomatillo yield of a non-early concentrated variety at 100 days after sowing, and/or (iv) a cumulative number of tomatillo fruits at least 5 times higher than the cumulative number of tomatillos of a non-early concentrated variety at 120 days after sowing.

In some embodiments, said early concentrated fruit set ideotype comprises (i) at least 70% of mature fruits at 60 days after transplanting, (ii) an harvest time comprised between 40 and 90 days after transplanting, (iii) a tomatillo yield at least 2.5 times higher than the tomatillo yield of a non-early concentrated variety at 60 days after transplanting, and/or (iv) a cumulative number of tomatillo fruits at least 5 times higher than the cumulative number of tomatillos of a non-early concentrated variety at 80 days after transplanting.

In some embodiments, said early concentrated fruit set ideotype comprises at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of mature fruits at 100 days after sowing or at 60 days after transplanting. A non-ideotype plant, i.e. a non-early concentrated tomatillo plant, will have 90% or more fruit that are not mature at the same harvest stage, i.e. at 100 days after sowing or at 60 days after transplanting. Thus, the tomatillo plant ideotype of the present invention has a more (or greater) uniform maturity (i.e. a large percentage of the plants producing marketable fruit at the time of harvest) when compared to the less or lack of uniform maturity of non-ideotype tomatillo plants, i.e. of non-early concentrated tomatillo plant.

In some embodiments, said harvest time in (ii) is comprised between 80 and 130 days after sowing, such as between 80 and 115 days after sowing, or between 95 and 115 days after sowing, or between 100 and 110 days after sowing. In some embodiments, said harvest time in (ii) is at 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 days after sowing.

In some embodiments, said harvest time in (ii) is comprised between 40 and 90 days after transplanting, such as between 40 and 75 days after transplanting, or between 55 and 75 days after sowing, or between 60 and 70 days after transplanting. In some embodiments, said harvest time in (ii) is at 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days after transplanting.

In some embodiments, said tomatillo yield in (iii) is at least 2.5, 3, 3.5, 4, 4.5, 5, 5.5, 6.5, 7, 7.5, 8, 8.5, 9, 9.5, 10, 15, 20, 25, 30, 35, 40, 45, 50, 75, or 100 times higher than the tomatillo yield of a non-early concentrated variety at 100 days after sowing or at 60 days after transplanting.

In some embodiments, said cumulative number of tomatillo fruits in (iv) is at least 5, 6, 7, 8, 9, 10, 15, 20, 25, 30, 35, 40, 45, 50, 75, or 100 times higher than the cumulative number of tomatillos of a non-early concentrated variety at 120 days after sowing or at 80 days after transplanting.

In some embodiments, said early concentrated fruit set ideotype further comprises (v) at least 80%, 81%, 82%, 83%, 84%, 85%, 86%, 87%, 88%, 89%, 90%, 91%, 92%, 93%, 94%, 95%, 96%, 97%, 98%, 99%, or 100% of mature fruits at 110 days after sowing or at 70 days after transplanting, (vi) a tomatillo yield at least 10, 15, 20, 25, 30, 35, 40, 45, 50, 75, or 100 times higher than the tomatillo yield of a non-early concentrated variety at 110 days after sowing or at 70 days after transplanting, (vii) a cumulative number of tomatillo fruits at least 50, 60, 70, 80, 90, or 100 times higher than the cumulative number of tomatillos of a non-early concentrated variety at 100 days after sowing or at 60 days after transplanting, (viii) a mean weight of fruits at least 7, 8, 9, 10, 20 times higher than the mean weight of fruits of a non-early concentrated variety at 100 days after sowing or at 60 days after transplanting, and/or (ix) a mean weight of fruits at least 10, 15, 20, 25, 30 times higher than the mean weight of fruits of a non-early concentrated variety at 110 days after sowing or at 70 days after transplanting.

In some embodiments, the tomatillo plant according to the invention further has an internode length comprised between 6 and 9 cm, such as between 6 cm and 7 cm.

In some embodiments the machine harvestable tomatillo plants of the present invention have a commercially acceptable fruit weight. In some embodiments machine harvestable tomatillos of the present invention have an average fruit weight greater than 65-70 grams per fruit at maturity.

In some embodiments, the machine harvestable tomatillo plant according to the invention further comprises at least 2 times more tomatillos with open husk than a non-early concentrated variety at maturity. In some embodiments, the machine harvestable tomatillo plant according to the invention has at least 2.5, 3, 3.5, 4, 4.5, 5, 5.5, 6.5, 7, 7.5, 8, 8.5, 9, 9.5, 10, 15, 20, 25, 30, 35, 40, 45, 50, 75, or 100 times more tomatillos with open husk than a non-early concentrated variety at maturity. In some embodiments, the machine harvestable tomatillo plant according to the invention has at least 50%, 55%, 60%, 65%, 70%, 75%, 80%, 85%, 90%, 95%, or 100% of tomatillos with open husk. In some embodiments, the machine harvestable tomatillo plant according to the invention has at least 50% of tomatillos with open husk.

Methods of Producing Tomatillo Plants with Machine Harvestable Traits and Other Desirable Agronomic Traits Any tomatillo plant with the machine harvestable traits of the present invention can be used to produce more tomatillo plants that have such machine harvestable traits through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

Choice of breeding or selection methods depends on the mode of plant reproduction, the heritability of the trait(s) being improved, and the type of cultivar used commercially (e.g., F1 hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Non-limiting breeding methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars; nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc).

Promising advanced breeding lines are thoroughly tested per se and in hybrid combination and compared to appropriate standards in environments representative of the commercial target area(s) for three years at least. The best lines are candidates for use as parents in new commercial cultivars; those still deficient in a few traits may be used as parents to produce new populations for further selection.

To select plants with desired agronomic traits, an elite control plant can be involved for comparison. Desired agronomic traits, such as fruit weight and fruit shape can be compared among the population under selection and the elite control plant.

In one embodiment, the evaluating step comprises visual observation to determine the severity of the pathogen infection, using a resistance scoring system. The resistance scoring system is well known in the art and is described elsewhere herein.

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hanauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA,* 99:9828-9832) and Quarrie et al. (Quarrie et al., Bulk segregant analysis with molecular markers and its use for improving drought resistance in maize, 1999, *Journal of Experimental Botany,* 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

Tomato Harvesting Equipment

Tomato harvesting machines have been used in harvesting tomato fruit in the field since at least 1949 (K. Coatney, Mar, 15, 2006, The machine that revolutionized a harvest, AgAlert, The Weekly Newspaper for California Agriculture). A number of different types of tomato harvesting equipment are commercially available. See, e.g., tomato harvesting machines available from California Tomato Machinery, Westside Equipment Company, Pomac, and Pik Rite. Examples of tomato harvesting machines are described in U.S. Pat. Nos. 4,232,506; 4,915,671; 5,685,773; 5,911,625; 6,003,293; 6,675,568; 7,051,505; 7,694,502; 7,581,375; and 7,921,628, each of which is incorporated herein in its entirety. When grower observation determines fruit are ready for harvest, the grower drives the harvester through the field. The harvester cuts the tomatillo vine as it drives through the field. The vines are lifted by mechanical conveyor into the heart of the harvester. Fruit shaken from the plant fall through a chain belt before being moved along a solid conveyor belt. Plant material is then blown off, leaving plant debris in the field and fruits in the harvest bin.

EXAMPLES

Example 1

Development of a Machine Harvestable Tomatillo

A. Development of TCS1 Hybrid

One of the most important grower needs is reducing the time to harvest that will potentially increase grower returns while reducing their inputs. So earliness was chosen as an important metric for new variety advancement.

In the first year, an F1 population, named PPC 511, obtained from the cross between the 04PM127-1 plant and Tehu plant, was sowed in Los Mochis, Mexico. Both 04PM127-1 and Tehu were selections from populations developed by mass breeding. Cross PPC 511 had extended habit and better fruit set than either parent. A bulk from the hybrid has been made; two hundred F2 plants were planted in Davis field in the second year. The majority of these plants had the typical tomatillo habit, namely long internodes and delayed setting. Approximately 4% of the plants segregated for a more compact habit. Plant 07PM 999-1 was selected for compact habit comprising of shorter plant height and shorter internode length. When grown in the third year in Los Mochis field, the plot from 07PM999-1 segregated compact and extended habit. We again selected plant with compact habit, i.e. plant MX PP461-1. In the fourth year, in Davis we grew and increased plot 08DPP 324-1 obtained from Mexican selection MX PP461-1. 08DPP 324-1 became the source to basic seed lot MS1 that bred true for compact habit. Subsequent test crosses with many different tomatillo inbred lines (see Table 1) confirm that line lot MS1 produces hybrids with (i) a determinate growth habit, (ii) a bush type growth habit, and (iii) an early concentrated fruit set ideotype. Accordingly and surprisingly, the ideotype of the plant according to the invention, namely the combination of determinate growth habit, bush type growth habit, and early concentrated fruit set ideotype, is acting as a dominant gene.

TABLE 1

Test crosses between the MS1 and tomatillos inbred lines.

| F1 | Female Habit | Female Source | Male Habit | Male Source | F1 Habit |
|---|---|---|---|---|---|
| TOH1 | Extended | TOH0 | Concentrated | MS1 | Concentrated, Open Husk |
| TCSB | Extended | S2 | Concentrated | MS1 | Concentrated |
| TCSC | Extended | S3 | Concentrated | MS1 | Concentrated |
| TCSD | Extended | S4 | Concentrated | MS1 | Concentrated |
| TCSE | Extended | S4 | Concentrated | MS1 | Concentrated |
| TCSF | Extended | S7 | Concentrated | MS1 | Concentrated |
| TCS1 | Extended | S8 | Concentrated | MS1 | Concentrated |

B. Development of TOH1 Hybrid

It has then be decided to add another trait, i.e. the open-husk character, to the plant according to the invention in order to develop tomatillo plants easier to use for the processing industry. The normal fruit ideotype for tomatillos is a fruit enclosed inside a fused husk (or calyx). When tomatillos flower the calyx is completely open. After fertilizations the calyx begins to close around the growing fruit. Indeed, early in the fruit ripening process the closed calyx or "husk" grows much faster than the newly formed fruit. At the end of maturation of the green fruit, the fruit completely fills the husk. Natural variants do occur where the fused husk sticks tightly to the fruit.

Processors of tomatillo fruit require their growers to remove the husk prior to shipping the fruit to the factory for processing. In supermarkets, tomatillos can be sold with or without husk. Typically tomatillos without husk are sold at a premium as significant hand labor is required.

During the breeding and selection of the TCS1 hybrid, an open husk character has been also segregating. It has thus been decided to add the open husk character to the concentrated set ideotype.

In the first year, in Los Mochis a four way hybrid made from two different sibling intermates from two bulk breeding populations (i.e. cross (116×116.3)×(108×108.2)) has been planted. Approximately 30% of the plants had open husk. Plant 08MEX PP 515 was selected and sent to Davis for generation advancement in summer of the first year. Selection 08DPP2660-1 segregated 25% plants with open husk. During the second year in Davis, a second selection for open husk has been made. Selection 09DPP 735-1 segregated 90% plants with open husk when planted to Mexico in the fourth year. Mexico selection 11MPP1135-1 had all plants with open husk and became the source to basic seed lot TOH0. TOH0 was then test crossed with our panel of inbreds. The most interesting hybrid resulting from these crosses was TOH1 hybrid made with the male line MS1 (see Table 1). TOH1 is a very early maturing, high yielding tomatillo hybrid. When picked with a machine harvester (tomato), hybrid TOH1 yields more than 85% of the fruit without husk. And also surprisingly, the open character is transmitted in a dominant manner.

Example 2

Harvest Trials

TCS1 and TOH1 hybrid are two representative tomatillo plants developed according to the invention. Each hybrid has the machine harvest tomatillo plant ideotype of the present invention, i.e. each hybrid has the determinate growth habit, the bush type growth habit and the early concentrated fruit set ideotype. The TOH1 hybrid further have the open husk phenotype as described above.

The commercially available Tamayo R, Tecozautla and Gran Esmerelda varieties were used as checks (i.e. non-early concentrated varieties) for their phenotype of tall plant structure and indeterminate plant growth.

TCS1 and TOH1 hybrids were evaluated in a machine harvest observational field trial in Davis, Cailf. The seeds were sowed on April 15th of the evaluation year, then seedlings were transplanted to the field on May 21th of the evaluation year, and the plants were harvested during a four week harvest period from July to August of the evaluation year. The climatic conditions were normal.

The TCS1 and TOH1 hybrid and the varieties Tamayo R, Gran Esmerelda and Tecozautla were first submitted to a pre-harvest assessment, and were analyzed for a variety of phenotypes including:

Determinacy—was assessed visually by comparing the growth and development of the tomatillo plants at throughout favorably growing conditions. Definitions for determinate and indeterminate growth were as previously described.

Plant Height—was measured vertically from the base of the stem at soil level to the most apical portion of the plant. Height was measured in centimeters (cm). Height is presented as an average of at least five consecutive plants per plot measured at harvest time from the soil to the top of the plant. Plant selection was made from the middle of the plot so that all plants measured were under normal growth competition.

Internode Length—was calculated by dividing the longest branch length by the number of internodes on that branch. Measurements are presented in centimeters (cm). Internode length was calculated from 5 randomly selected consecutive plants.

Open husk—was assessed visually on the plant by looking for husks (calyxes) that were at least 50% open. Open husks in our machine harvest trial were also measured by randomly selecting 50 fruits harvested into a bin from a 50 foot plot. We then counted the number of fruits without husk out of the 50 were then counted. The results of the pre-harvest assessment are presented in Table 2 below. Tomatillos hybrids TCS1 and TOH1 produced according to the present invention exhibited determinate growth phenotypes and bush type growth habit.

TABLE 2

Pre-harvest date collected from Davis field tomatillo trial on the evaluation year.

| Plants | Determinacy | Growth habit | Open Husk | Plant height (cm) | Mean Branch length (cm) | Mean internode length (cm) |
|---|---|---|---|---|---|---|
| Check variety | Indeterminate | Extended | No | 84 | 112.2 | 7.2 |
| TCS1 | Determinate | Bush type | No | 52 | 99.7 | 6.5 |
| TOH1 | Determinate | Bush type | Yes | Non available | Non available | Non available |
| Prob > F | Non applicable | Non applicable | Non applicable | <0.0001 | 0.0144 | 0.0926 |

The TOH1 hybrid has significantly much more tomatillos fruits with open husk than the check varieties Tamayo R, Tecozautla and Gran Esmerelda as shown in Table 3 below.

TABLE 3

Comparison of Means and Standard Deviations for Check Variety with closed husk character and TOH1 hybrid, an Open Husk plant, for Open Husk Trait.

| Variety Type Husk | Number | Mean Percent Open Husk | F Ratio | Prob > F |
|---|---|---|---|---|
| Closed | 24 | 40.5% | 52.9 | <0.0001 |
| Open | 6 | 89% | | |

Then the TCS1 and TOH1 hybrids and the varieties Tamayo R, Gran Esmerelda and Tecozautla were harvested, and harvesting was assessed by quantifying various yield and fruit quality factors as described below:

Matured Fruit Percentage—corresponds to the number of matured fruits as a percentage of all tomatillo fruits on the plants. Percentage was calculated based on fruit counts for all growing plants of a particular variety. Maturity was determined by visually inspecting collected fruits. Mature tomatillos (i.e., mature fruits) were defined as tomatillos having reached their mature firmness, size, and shape expected for their variety. Typically in the field this is seen as tomatillos with fruit filling the capsule created by the husk. Mature tomatillos did not have to exhibit color changes to be considered mature.

Yield—measured by weighing the fruit harvest from five plants in the center of the plot. Fruit weight, fruit count and maturity were determined from these harvested fruits. Results were presented as kilograms harvested from the plot, number of fruit harvested from the plot, number of mature fruit in the harvest.

Tomatillo Fruit Weight—was calculated by dividing the kilograms harvested by the number of fruit in the harvest.

Cumulative tomatillo fruit number—was calculated by adding the fruit from each harvest described above (i.e. four week harvest period from July to August) in the yield section to a cumulative total for the plot. Cumulative yield is a weigh to portray concentration, i.e. varieties whose first two picks represent the majority of the yield are considered concentrated.

Figure 1:
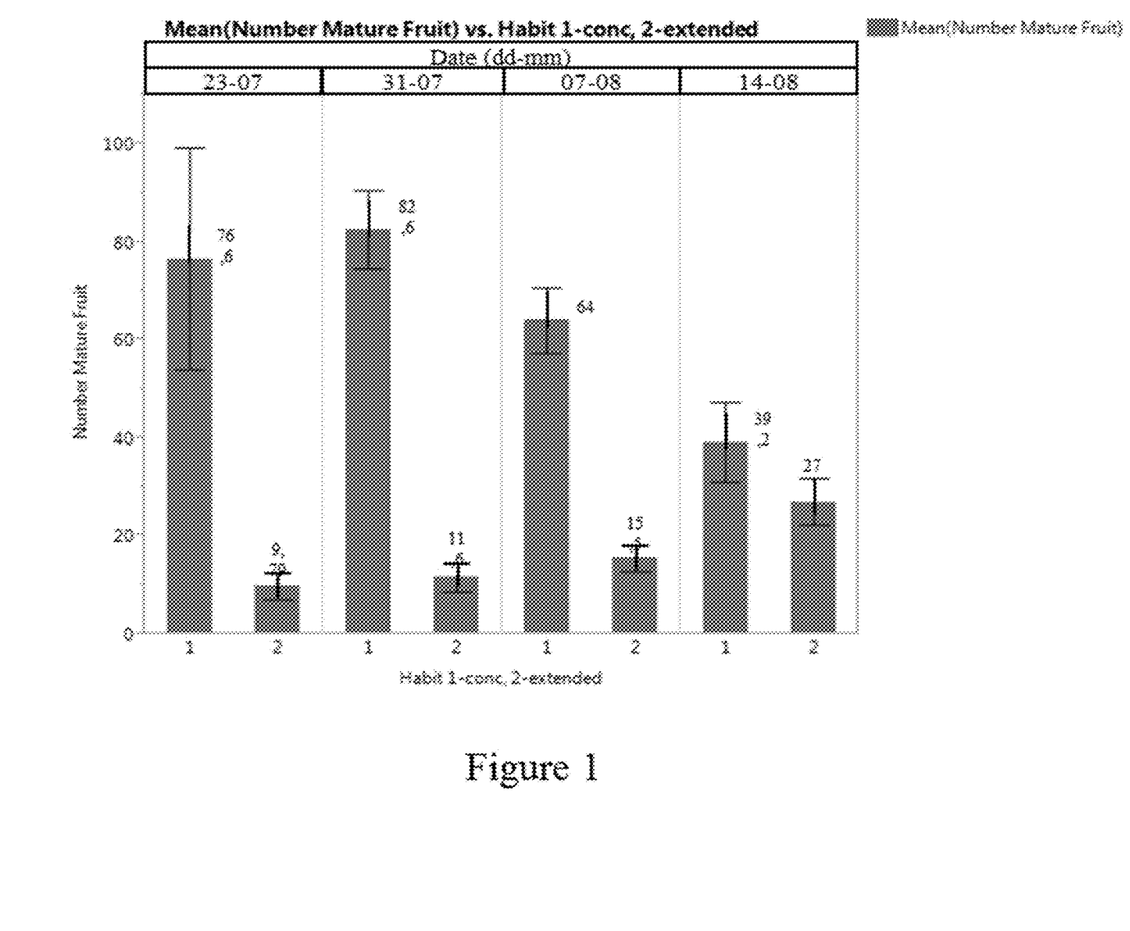
FIG. 1 represents the mean number of mature fruits harvested from tomatillo plants according to the invention (1-concentrated) or the check variety (2-extended, i.e. non-early concentrated variety) in a period of four weeks starting 100 days after sowing or 60 days after transplant to field. For each harvest date all mature fruits from five different consecutive plants were harvested.
Figure 2:
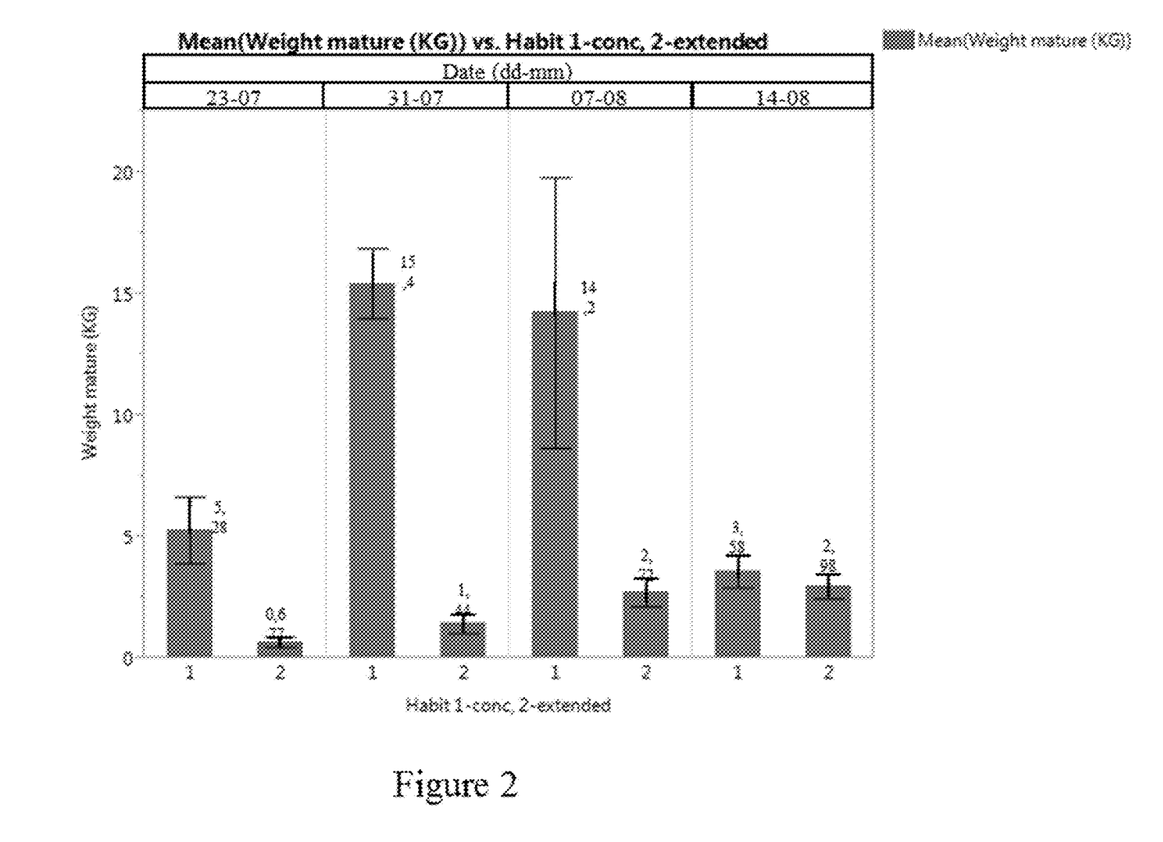
FIG. 2 represents the mean weight of all mature fruits harvested from either the ideotype tomatillo plant according to the invention (1-concentrated) or the check variety (2-extended, i.e. non-early concentrated variety) in a period of four weeks starting starting 100 days after sowing or 60 days after transplant to field. For each harvest date all fruit from five different consecutive plants were harvested. The fruits were then separated in two bins according to their maturity, i.e. by separating mature and immature fruits, counted and weighted in each bin.
Figure 3:
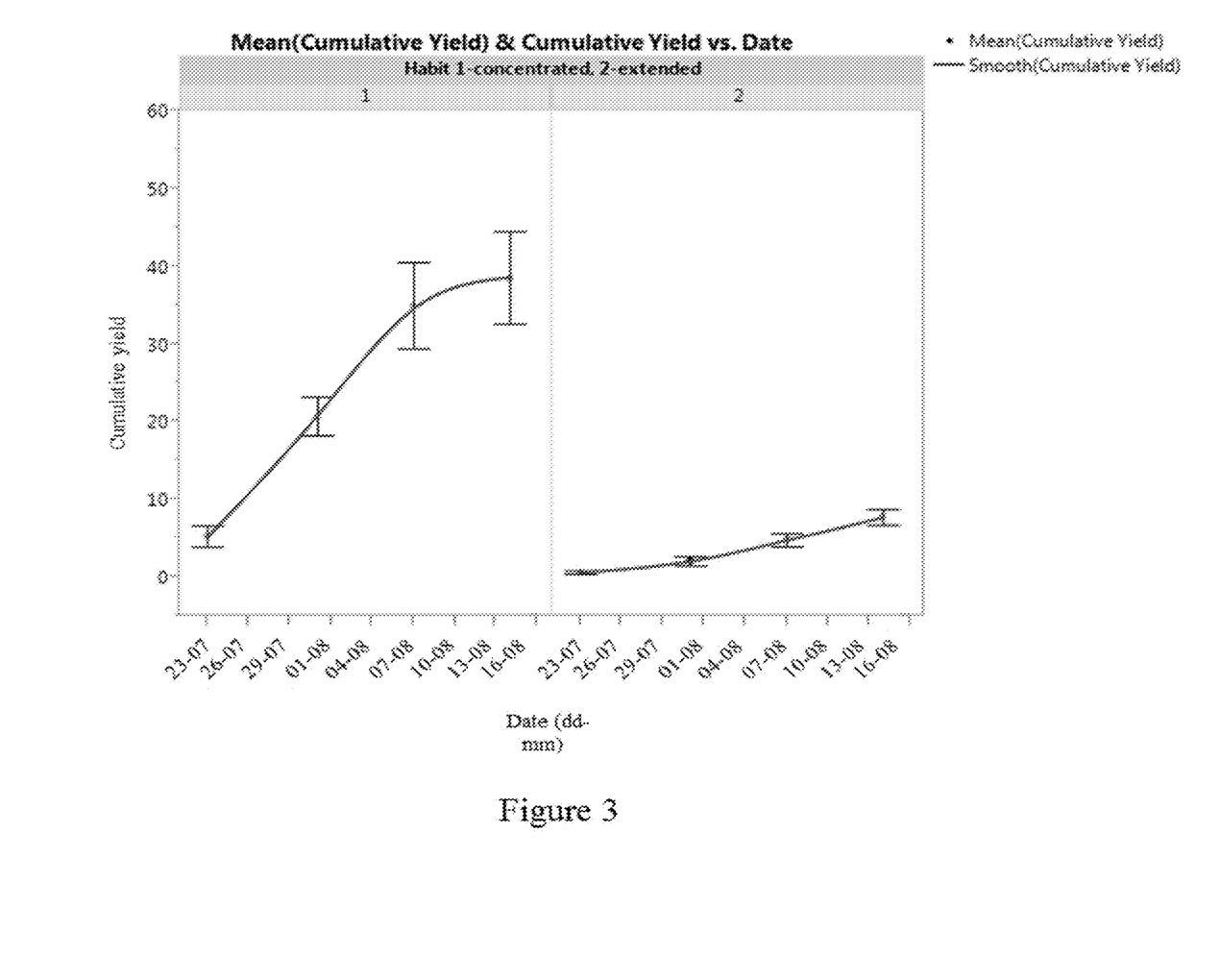
FIG. 3 represents the mean cumulative yield of fruits of the ideotype tomatillo plant according to the invention (1-concentrated) and the check variety (2-extended, i.e. non-early concentrated variety) in a period of four weeks starting 100 days after sowing.
Figure 4:
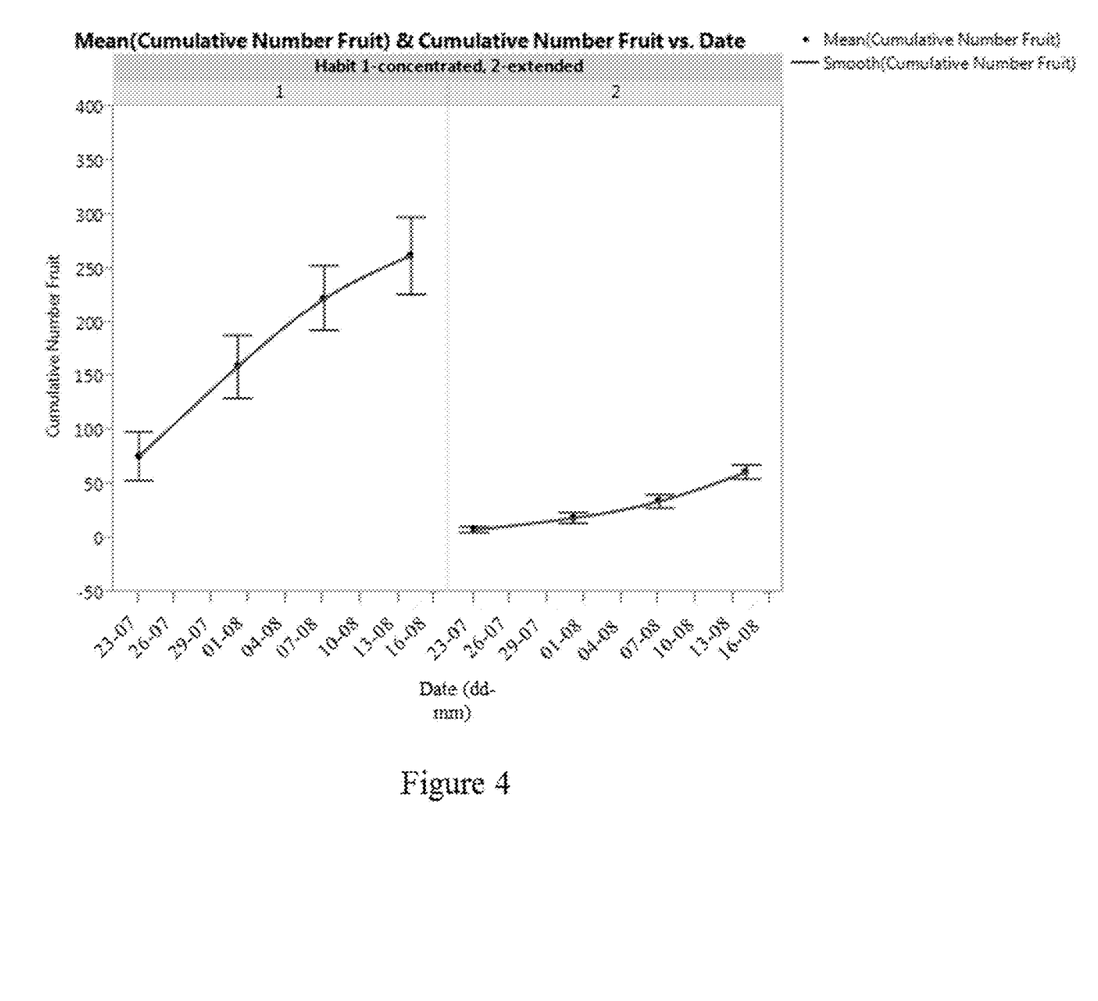
FIG. 4 represents the mean cumulative number of fruits of the ideotype tomatillo plant according to the invention (1-concentrated) and the check variety (2-extended, i.e. non-early concentrated variety) in a period of four weeks starting 100 days after sowing.

Results of harvest at each weeks are presented in the FIGS. 1 to 4.

The TCS1 hybrid yields more tomatillos in less time than the check varieties Tamayo R, Tecozautla and Gran Esmerelda. The TCS1 hybrid also yields more at each harvest and in total during the four weeks harvest period. When mature fruits (i.e. market ready fruits) are weighted and counted, the TCS1 hybrid produces significantly more than the check varieties Tamayo R, Tecozautla and Gran Esmerelda.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. It should be understood that the examples and embodiments described herein are for illustrative purposes only and that various modifications or changes in light thereof will be suggested to persons skilled in the art and are to be included within the spirit and purview of this application.

DEPOSIT INFORMATION

A deposit of the tomatillo seeds of this invention is maintained by HM. CLAUSE, Inc. Davis Research Station, 9241 Mace Boulevard, Davis Calif. 95618. In addition, a sample of the tomatillo seeds of this invention has been deposited by HM. CLAUSE, Inc., 28605 Country Road 104, Davis, Calif. 95618, with the National Collections of Industrial, Food and Marine Bacteria (NCIMB), 23 St Machar Drive, Aberdeen, Scotland, AB24 3RY, United Kingdom. HM. CLAUSE, Inc. has authorized the applicant to refer to the deposited biological material in the application.

To satisfy the enablement requirements of 35 U.S.C. § 112, and to certify that the deposit of the seeds of the present invention meets the criteria set forth in 37 C.F.R. § § 1.801-1.809, Applicants hereby make the following statements regarding the deposited tomatillo seed 'TCS1', and 'TOH1' (deposited as NCIMB Accession Nos. 42413 and 42412, respectively):

1. During the pendency of this application, access to the invention will be afforded to the Commissioner upon request;

2. Upon granting of the patent the seeds will be available to the public under conditions specified in 37 CFR 1.808;

3. The deposit will be maintained in a public repository for a period of 30 years or 5 years after the last request or for the enforceable life of the patent, whichever is longer; and 4. The viability of the biological material at the time of deposit will be tested; and 5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same seed source with the NCIMB.

The invention claimed is:

1. A seed of tomatillo plant designated TCS1, wherein a representative sample of seed of said machine harvestable tomatillo plant has been deposited under NCIMB No. 42413.

2. A seed of tomatillo plant designated TOH1, wherein a representative sample of seed of said machine harvestable tomatillo plant has been deposited under NCIMB No. 42412.

3. A tomatillo plant, or a part thereof or a plant cell thereof, produced by growing the seed of claim 1 or claim 2.

4. The tomatillo plant, or a part thereof or a plant cell of claim 3, wherein the plant part is a seed, a fruit, a reproductive material, roots, flowers, a rootstock or a scion.

5. The tomatillo plant, or a part thereof or a plant cell of claim 3, wherein the plant cell is a regenerable cell.

6. A tissue culture of regenerable cells produced from the plant or plant part of claim 3, wherein a plant regenerated from the tissue culture has all of the morphological and physiological characteristics of tomatillo plant TCS1 or TOH1 when grown in the same environmental conditions and wherein a representative sample of seed of TCS1 has been deposited under NCIMB No. 42413, and a representative sample of seed of TOH1 has been deposited under NCIMB No. 42412.

7. A machine harvestable plant regenerated from the tissue culture of claim 6, said plant having all of the morphological and physiological characteristics of tomatillo plant TCS1 or TOH1 when grown in the same environmental conditions, and wherein a representative sample of seed of TCS1 has been deposited under NCIMB No. 42413, and a representative sample of seed of TOH1 has been deposited under NCIMB No. 42412.

8. A tomatillo plant seed or a tomatillo fruit produced from the plant of claim 3.

9. A method for producing a tomatillo seed, comprising self-pollenating the tomatillo plant of claim 3 and harvesting the resultant tomatillo seed.

10. A tomatillo seed produced by the method of claim 9.

11. A method for producing a tomatillo plant, comprising crossing a first parent tomatillo plant with a second parent tomatillo, wherein said first parent tomatillo plant and/or second parent tomatillo plant is the tomatillo plant of claim 3.

12. A method of producing a tomatillo plant derived from tomatillo plant TCS1 or tomatillo plant TOH1, the method comprising the steps of:
(a) crossing the plant of claim 3 with a second tomatillo plant to produce a progeny plant.

13. The method of claim 12, wherein the method further comprises
(b) crossing the progeny plant of step (a) with itself or a second tomatillo plant to produce a seed;
(c) growing a progeny plant of a subsequent generation from the seed produced in step (b); and
(d) crossing the progeny plant of a subsequent generation of step (c) with itself or a second tomatillo plant to produce a tomatillo plant derived from tomatillo plant TCS1 or TOH1.

14. The method of claim 13, further comprising the step of:
(e) repeating step b) and/or c) for at least 1 more generation to produce a tomatillo plant derived from tomatillo plant TCS1 or TOH1.

15. A method for producing a tomatillo seed, comprising self-pollinating the tomatillo plant of claim 3 at least once to produce a progeny plant and harvesting a tomatillo seed from the progeny plant.

16. A method of producing tomatillos, said method comprising:
a. placing a seed from the tomatillo plant of claim 3 in an environment conducive to germination,
b. allowing said seed to germinate into a plant, and
c. allowing said plant to produce tomatillos.

17. A method of harvesting tomatillos, said method comprising harvesting the fruit of a mature tomatillo plant using a harvesting machine, wherein the mature tomatillo plant that is harvested is the tomatillo plant of claim 3.

18. A food product obtained from the fruit of claim 8, wherein the food product comprises a plant cell of hybrid tomatillo plant designated TCS1 or hybrid tomatillo plant designated TOH1.

19. The food product of claim 18, wherein said food product is selected from the group consisting of fresh fruits and pickled fruits.

20. A method of producing a food product, comprising processing the fruit of claim 8 into the food product.

* * * * *